(12) United States Patent
Keegan et al.

(10) Patent No.: US 10,061,739 B2
(45) Date of Patent: Aug. 28, 2018

(54) PORTABLE INSTRUMENT AND DOCKING STATION WITH DIVIDED UNIVERSAL SERIAL BUS COMMUNICATION DEVICE

(71) Applicant: Welch Allyn, Inc., Skaneateles Falls, NY (US)

(72) Inventors: Christopher M. Keegan, Marcellus, NY (US); Kenneth V. Coon, Jordan, NY (US); Christopher M. Haigney, Syracuse, NY (US); Miguel C. Mudge, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 56 days.

(21) Appl. No.: 15/084,678

(22) Filed: Mar. 30, 2016

(65) Prior Publication Data

US 2016/0210262 A1    Jul. 21, 2016

Related U.S. Application Data

(63) Continuation of application No. 13/740,455, filed on Jan. 14, 2013, now Pat. No. 9,330,046.

(51) Int. Cl.
| | | |
|---|---|---|
| *G06F 13/42* | (2006.01) | |
| *G06F 13/40* | (2006.01) | |
| *G06F 13/38* | (2006.01) | |
| *G06F 1/16* | (2006.01) | |
| *G06F 19/00* | (2018.01) | |

(52) U.S. Cl.
CPC ........ *G06F 13/4286* (2013.01); *G06F 13/385* (2013.01); *G06F 13/4081* (2013.01); *A61B 2560/0456* (2013.01); *G06F 1/1632* (2013.01); *G06F 19/3418* (2013.01)

(58) Field of Classification Search
CPC ..... G06F 1/1632; G06F 1/1626; G06F 1/1613
See application file for complete search history.

(56) References Cited

U.S. PATENT DOCUMENTS

| | | |
|---|---|---|
| 6,393,431 B1 | 5/2002 | Salvati |
| 6,770,028 B1 | 8/2004 | Ali |
| | (Continued) | |

FOREIGN PATENT DOCUMENTS

| | | |
|---|---|---|
| DE | 198 14 356 A1 | 10/1999 |
| DE | 20 2005 000 172 U1 | 4/2005 |
| | (Continued) | |

OTHER PUBLICATIONS

PCT International Searching Authority, International Search Report and Written Opinion for International Application No. PCT/US2013/078495, dated May 16, 2014, 10 pages.

(Continued)

*Primary Examiner* — Brian T Misiura
(74) *Attorney, Agent, or Firm* — Merchant & Gould P.C.

(57) ABSTRACT

A universal serial bus (USB) communication system includes a portable instrument and a docking station that communicate with a host device using a divided USB communication device. A first portion of the USB communication device is provided in the portable instrument. A second portion of the USB communication device is provided in the docking station. The first portion includes a non-USB communication device that communicates with the second portion in a non-USB format. The second portion converts the communications into a USB format suitable for the host device.

18 Claims, 9 Drawing Sheets

(56) References Cited

U.S. PATENT DOCUMENTS

| | | |
|---|---|---|
| 7,188,621 B2 | 3/2007 | De Vries |
| 7,386,868 B2 | 6/2008 | McCormack |
| 7,530,949 B2 | 5/2009 | Al Ali |
| 7,575,555 B1 | 8/2009 | Bryant |
| 7,787,014 B2 | 8/2010 | Serceki |
| 7,873,772 B2 | 1/2011 | Waldhoff |
| D631,869 S | 2/2011 | Yamamoto |
| 7,976,337 B1 | 7/2011 | Cortopassi et al. |
| 8,214,566 B2 | 7/2012 | Edwards et al. |
| D675,157 S | 1/2013 | Lacotta et al. |
| 8,694,085 B2 | 4/2014 | Reifman |
| 9,081,903 B2 | 7/2015 | Blondi et al. |
| 2004/0147818 A1 | 7/2004 | Levy |
| 2005/0262285 A1 | 11/2005 | Kang |
| 2006/0026326 A1 | 2/2006 | Hunt et al. |
| 2006/0039105 A1 | 2/2006 | Smith et al. |
| 2006/0199997 A1 | 9/2006 | Hassler et al. |
| 2008/0015423 A1 | 1/2008 | Lam et al. |
| 2008/0183910 A1 | 7/2008 | Natoli et al. |
| 2009/0005651 A1 | 1/2009 | Ward et al. |
| 2010/0076348 A1 | 3/2010 | McNames et al. |
| 2010/0145146 A1 | 6/2010 | Melder |
| 2011/0022748 A1 | 1/2011 | Edwards et al. |
| 2012/0190406 A1 | 7/2012 | Chen |
| 2012/0302288 A1 | 11/2012 | Born et al. |
| 2012/0303331 A1 | 11/2012 | Niemczak et al. |

FOREIGN PATENT DOCUMENTS

| | | |
|---|---|---|
| KR | 20-0425-912 | 9/2006 |
| KR | 10-2010-0055261 A | 5/2010 |

OTHER PUBLICATIONS

Datalogic ADC—Mobile, http://www.geminicomputersinc.com/dtl-95a151047.html, 4 pages (Date Accessed: Jun. 7, 2012).

Unitech MCA Single Slot Cradle Docking Cradle—PC, http://www.google.com/products/catalog?q=dock+USB=medical&cid=13566751733166147532&os=tech-specs, 2 pages (Date Accessed: Jun. 7, 2012).

PORTABLE INSTRUMENT AND DOCKING STATION WITH DIVIDED UNIVERSAL SERIAL BUS COMMUNICATION DEVICE

CROSS-REFERENCE TO RELATED APPLICATION

This application is a continuation of U.S. patent application Ser. No. 13/740,455 filed on Jan. 14, 2013, issued on May 3, 2016 as U.S. Pat. No. 9,330,046, and entitled PORTABLE INSTRUMENT AND DOCKING STATION WITH DIVIDED UNIVERSAL SERIAL BUS COMMUNICATION DEVICE, the disclosure of which is hereby incorporated by reference in its entirety.

BACKGROUND

Various techniques exist for transmitting data between electronic devices. One common technique is referred to as serial data communication. Serial communication typically involves the transmission of data in a data stream, one bit at a time. The data is typically transmitted across a single conductor at a specified baud rate with high and low voltage levels representing bits ("0" or "1") of the data stream. Some serial communication standards utilize start and stop bits to signal the beginning and end of each byte (8 bits) of data.

Another common technique is referred to as Universal Serial Bus (USB) data communication. USB is commonly used both to communicate data between electronic devices and also to supply power from one of the devices to the other. The USB data communication standards require the transmission of various messages back and forth between the electronic devices, and therefore require that such devices have increased processing capabilities than basic serial communication devices. As a result, an electronic device that utilizes USB data communication may be more expensive and complex than an electronic device that utilizes serial data communication.

SUMMARY

In general terms, this disclosure is directed to a USB communication device. In one possible configuration and by non-limiting example, the USB communication device is divided between a first portion arranged in a portable instrument, and a second portion arranged in a docking station.

One aspect is a docking station comprising: a housing having a receptacle formed therein, the receptacle sized and configured to receive and support at least a portion of a portable medical instrument and including electrical contacts arranged to electrical connect with the portable medical instrument, wherein the portable medical instrument includes a first portion of a USB communication device adapted to communicate in a serial data communication format; and a second portion of the USB communication device enclosed in the housing, the second portion comprising: a serial to USB converter arranged in the housing and electrically connected to the electrical contacts, wherein the serial to USB converter is arranged and configured to convert between the serial data communication format and a USB data communication format to facilitate communication between the portable medical instrument and a host device; and electronic circuitry that detects the electrical connection of the portable medical instrument with the electrical contacts and initiates the communication with the host device after detecting the electrical connection.

Another aspect is a portable medical instrument comprising: instrument electronics adapted to generate data associated with a physiological characteristic of an individual; and a first portion of a USB communication device, the first portion comprising: a processing device, the processing device programmed to generate messages in accordance with a USB data communication protocol, at least one of the messages including the data; and a serial communication device that receives the messages from the processing device and transmits the messages to a docking station in a non-USB serial data communication format.

A further aspect is a dockable instrument assembly including a divided universal serial bus (USB) communication device configured to communicate with a USB-enabled host device, the dockable instrument assembly comprising: a portable instrument comprising: instrument electronics operable to generate data to be communicated to the host device, the data being associated with a physiological characteristic of an individual; and a first portion of the divided USB communication device comprising a serial communication device, wherein the first portion is arranged and configured to receive the data from the instrument electronics and transmit the data in a serial format with the serial communication device; and a docking station comprising: a receptacle sized to receive at least a portion of the portable instrument therein; a second portion of the divided USB communication device, the second portion comprising a serial to USB converter arranged and configured to: detect when the portable instrument is inserted into the receptacle; after detecting insertion of the portable instrument into the receptacle, initiate communication with the host device; and facilitate communication between the portable instrument and the host device.

Yet another aspect is a method of communicating with a USB-enabled host device, the method comprising: monitoring for insertion of a portable medical instrument into a docking station; detecting the insertion of the portable medical instrument into the docking station, the portable medical instrument configured to communicate with the docking station through a non-USB data communication device in a non-USB format; after detecting the insertion of the portable medical instrument, initiating communication with the host device to alert the host device to an arrival of the portable medical instrument; and facilitating communication between the portable medical instrument and the host device.

DETAILED DESCRIPTION

Figure 1:
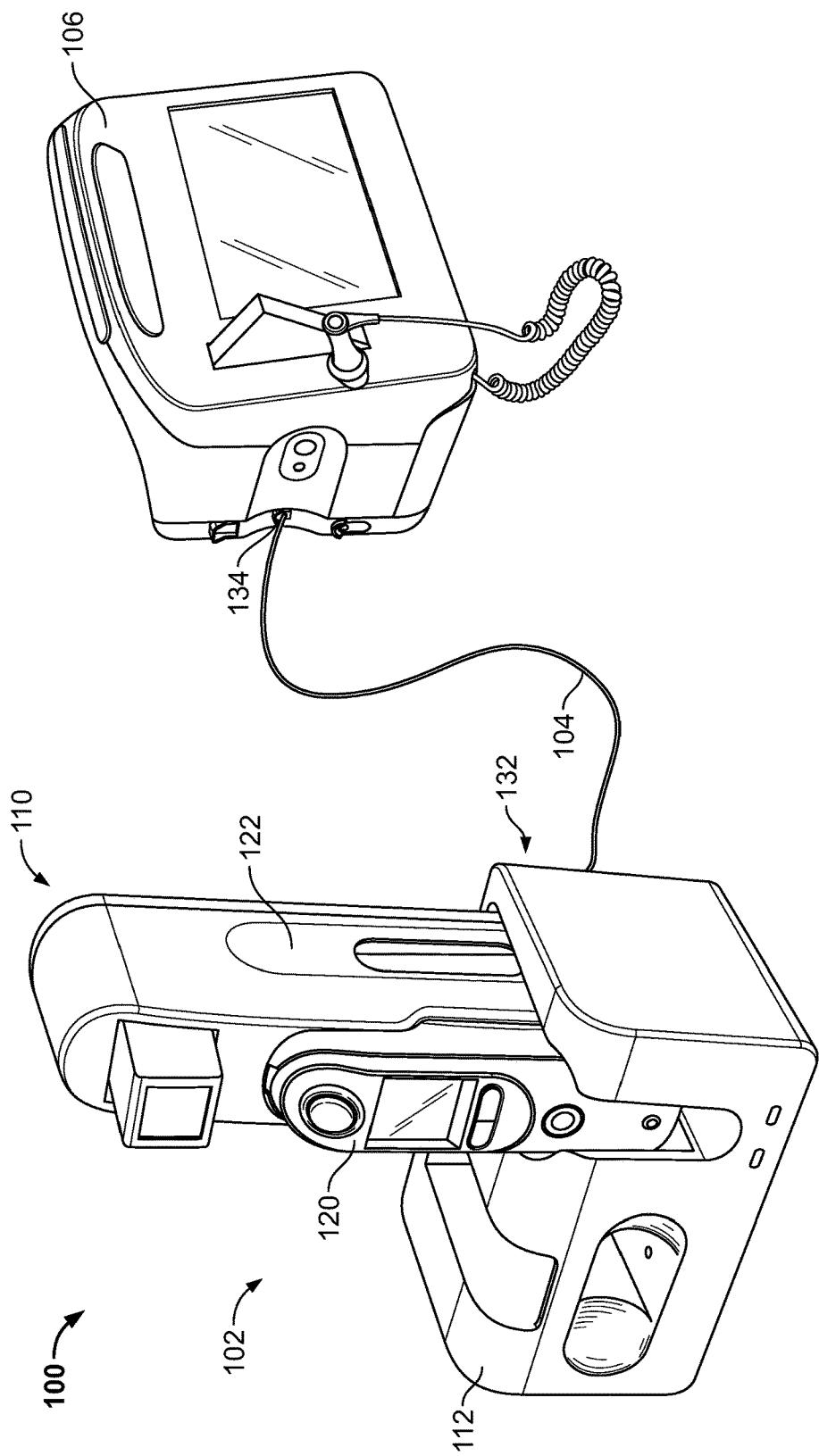
FIG. 1 is a perspective view of an example USB communication system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

As discussed above, the USB data communication standard defines hardware requirements (including hardware requirements for cables and connectors) and data communication protocols for communicating data between two or more electronic devices. In order to conform to the USB data communication standards, a USB communication device will typically have more intelligence (i.e., processing capabilities) than communication devices configured to communicate using other data communication standards, such as serial communication. Serial communication typically permits data to be communicated from one device to another with a simple stream of bits, for example. As a result, the USB data communication standards require USB-enabled devices to have at least a minimal level of intelligence, which can increase the cost, size, and complexity of such devices.

In one example, the present disclosure describes a USB-enabled device in which the communication electronics are divided into two or more portions. A first portion communicates using a serial data communication device according to a serial data communication protocol. The second portion converts the serial data communication into a form required to communicate according to a USB data communication protocol. This permits the first portion to have reduced cost and complexity, for example. The first portion is able to communicate with a USB-enabled host device using the second portion.

FIG. 1 is a perspective view of an example USB communication system 100. In this example, the Universal Serial Bus (USB) communication system 100 includes a dockable instrument assembly 102, a USB cable 104, and a host device 106. The example dockable instrument assembly 102 includes a portable instrument 110 and a docking station 112. The example portable instrument 110 includes an instrument 120 and a cradle 122. The docking station 112 includes a USB port 132 that receives and connects with a plug of the USB cable 104. The host device 106 also includes a USB port 134 that receives and connects with a plug at the other end of the USB cable 104.

The dockable instrument assembly 102 is a device capable of communicating with the USB-enabled host device 106 according to one or more USB data communication protocols. In this example, the dockable instrument assembly 102 includes at least two components, including a portable instrument 110 and a docking station 112.

The portable instrument 110 is an electronic device that generates data to be communicated to the host device 106. In some embodiments, the portable instrument 110 is or includes an instrument 120.

In some embodiments, the portable instrument 110 is single device enclosed in a single housing. However, in the example shown in FIG. 1, the portable instrument 110 includes two separate parts. More specifically, the portable instrument 110 includes an instrument 120 and a cradle 122. Other embodiments of the portable instrument 110 include more than two parts.

The instrument 120 is a device that generates and stores data, and it is desired that such data be transferred to the host device 106. An example of an instrument 120 is a medical instrument configured to measure or detect at least one characteristic of a patient. An example of a medical instrument is a thermometer. An example of a thermometer is an infrared ear thermometer. Other medical instruments are used in other embodiments. Several additional examples of medical devices include a digital otoscope, a digital opthalmoscope, and a hand held imaging device. Other non-medical instruments are used in yet other embodiments. In this example, the portable instrument 110 also includes a cradle 122. The cradle 122 is a handheld storage unit that supports the instrument 120 when the instrument is not in use. The cradle 122 also includes additional storage compartments, in some embodiments, for storing accessories for use with the instrument 120, such as disposable probe covers. In some embodiments, the cradle 122 includes electrical contacts that connect with corresponding electrical contacts on the instrument 120 when the instrument 120 is placed into the cradle 122. The electrical contacts permit data and/or power to be transferred between the cradle 122 and the instrument 120. In other possible embodiments, however, the portable instrument 110 does not include the cradle 122, and the instrument 120 can be docked directly into the docking station 112, for example.

The docking station 112 is a support device that temporarily stores the portable instrument 110 when the portable instrument 110 is not being used by a user. The docking station can be placed on a desk, table, counter top, or other horizontal structure, for example, or can be mounted to a wall or other vertical structure. The docking station 112 typically includes a receptacle sized to receive the portable instrument 110. In some embodiments, the docking station 112 electrical contacts arranged in the receptacle. The electrical contacts make contact with corresponding contacts on the portable instrument 110 for charging the portable instrument 110 and/or for data communication. The docking station 112 includes a USB port 132 that receives and connects with a plug of the USB cable 104.

The USB cable 104 includes electrical conductors and conforms to the USB standards for USB data communication cables.

The host device 106 is an electronic device that receives data from the portable instrument 110 utilizing USB data communication. In the illustrated example, the host device 106 is a vital signs monitor. An example of a vital signs monitor is the CONNEX vital signs monitor available from Welch Allyn, Inc. of Skaneateles Falls, N.Y. Is another example, the host device 106 is a computing device, such as a desktop computer, a laptop computer, a mobile computing device (including a smartphone, tablet computer, etc.), or other device including a processor and computer readable storage media, wherein the processor is capable of processing data instructions stored in the computer readable storage media. The host device also includes a USB port 134 that receives and connects with a plug at the other end of the USB cable 104.

Figure 2:
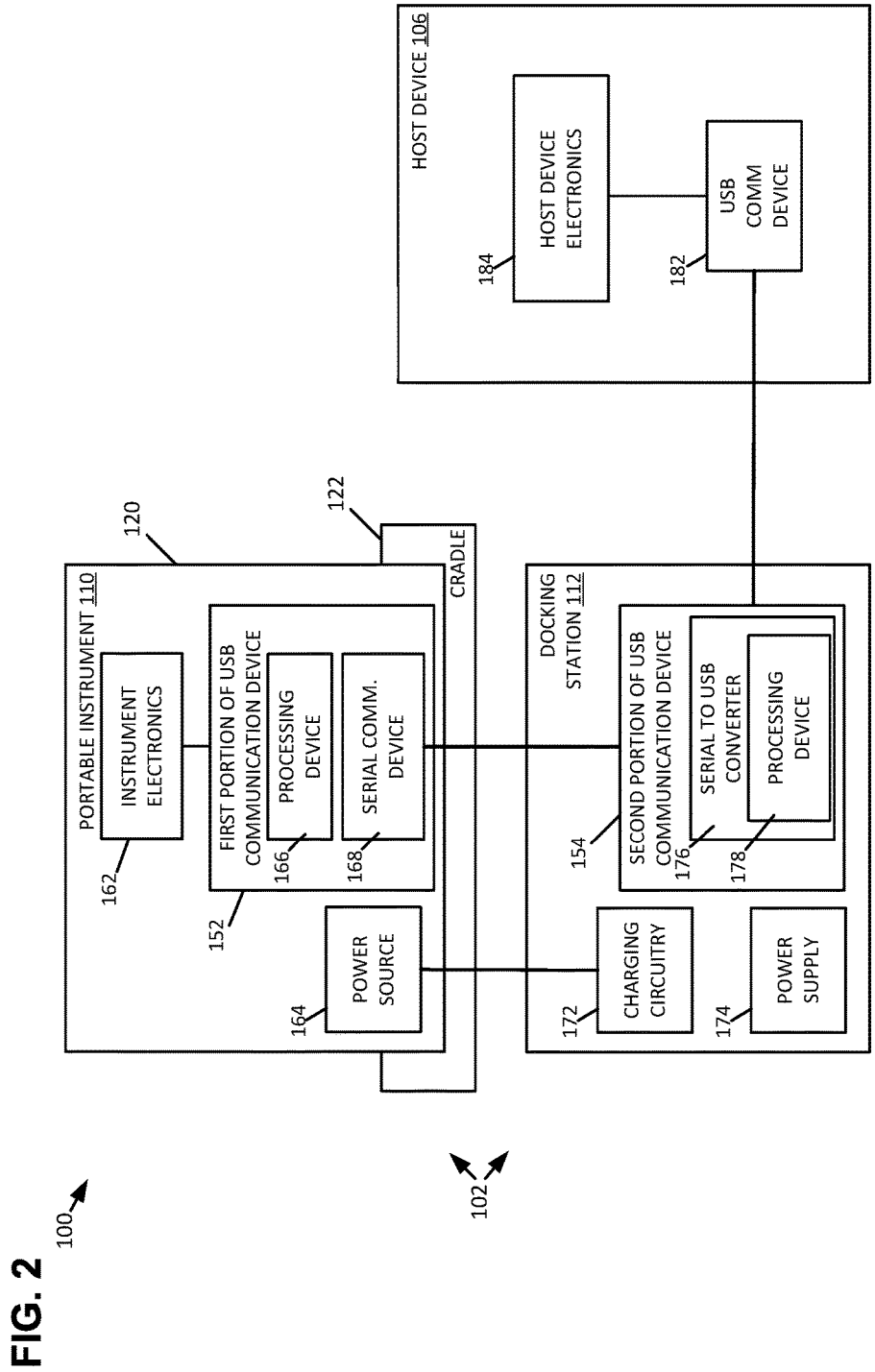
FIG. 2 is a schematic block diagram illustrating another example of the USB communication system shown in FIG. 1, including a divided USB communication device.

FIG. 2 is a schematic block diagram illustrating another example of the USB communication system 100 shown in FIG. 1.

Similar to the example shown in FIG. 1, this example shown in FIG. 2 also includes the dockable instrument assembly 102, the USB cable 104, and the host device 106. The dockable instrument assembly 102 includes the portable instrument 110 and the docking station 112. The portable instrument 110 includes the instrument 120 and the cradle 122, though some portable instruments 110 do not include a cradle 122.

More specifically, the example shown in FIG. 2 illustrates a divided USB communication device in which a first portion 152 of the USB communication device is part of the portable instrument 110, while a second portion 154 of the USB communication device is part of the docking station 112.

FIG. 2 also illustrates additional example components of the USB communication system 100. For example, the portable instrument 110 includes instrument electronics 162 and power source 164, and the first portion 152 of the USB communication device includes a processing device 166 and a serial communication device 168. The docking station 112 includes charging circuitry 172 and a power supply 174, and the second portion 154 of the USB communication device includes a serial to USB converter 176, which itself includes a processing device 178.

Before discussing the USB communication device in further detail, the other example components of the portable instrument 110, docking station 112, and host device 106 are discussed below.

The portable instrument 110 (including the instrument 120) operates to perform a desired function, and includes instrument electronics 162 that perform that function. For example, in some embodiments the instrument 120 is a thermometer. In this example, the instrument electronics 162 operate to determine a temperature of a patient. When the thermometer is an infrared thermometer, for example, the instrument electronics 162 include an infrared emitter and detector, and electronics suitable for determining a temperature of the patient from detected infrared signals. A wide variety of other instruments can be utilized in other embodiments. The instrument electronics 162 typically include some type of processing device and a computer readable storage device that stores program instructions, which can be processed by the processing device to perform the appropriate operations defined by the program instructions. Further, many embodiments include at least some type of sensor, which operates to detect a property, characteristic, or event, and generate data associated with the sensor. In typical embodiments, the instrument 110 operates to generate data for transmission to the host device 106, and such data is transmitted utilizing the divided USB communication device described herein.

The power source 164 stores energy to power the electronic components of the portable instrument 110 when the portable instrument 110 is turned on and disconnected from the docking station. An example of a power source 164 is a battery. Another example of a power source is a super capacitor. Multiple power sources or combinations of power sources are included in yet other embodiments.

In some embodiments the portable instrument 110 is associated with a cradle 122. For example, in some embodiments the instrument 120 housed in the cradle 122 when it is not in use. The cradle 122 can also store accessories or other components used with the portable instrument 110. In some embodiments, the cradle 122 includes electrical contacts and electrical conductors to transfer signals between the instrument 120 and the docking station 112 when the portable instrument 110 is inserted into the docking station.

The cradle 122 can also include one or more electronic components, such as a pull-down resistor electrically connected with two or more of the electrical conductors, as described in more detail herein. In other possible embodiments, the cradle 122 includes no electronic components, other than contacts and conductors.

In some embodiments, the portable instrument 110 does not include a cradle 122. For example, the instrument 120 can be inserted directly into the docking station 112 where direct electrical contact is made between the instrument 120 and the docking station 112. In some embodiments the charging circuitry 172 detects a charge status of the power source 164 and provides power according to the detected charge status. For example, if the power source 164 is not fully charged, the charging circuitry 172 can operate in a fast charging mode, while the charging circuitry 172 operates in a trickle charge mode when the power source 164 is detected to be fully charged.

In some embodiments, the docking station 112 includes charging circuitry 172 that operates to recharge the power source 164 when the portable instrument 110 is inserted into the docking station 112. The charging circuitry 172 is powered by a power source, such as the power supply 174. In some embodiments, the power supply 174 is a battery or a super capacitor. In other embodiments, the power supply 174 receives power from an external power source, such as mains power, and operates to convert the received power into a form suitable for delivery to the charging circuitry 172 and other electronic components of the docking station 112.

The host device 106 includes a USB communication device 182 that communicates with the divided USB communication device of the dockable instrument assembly 102, such as to receive data generated by the instrument electronics 162.

The host device 106 also includes host device electronics 184 that operate to perform the desired functions of the host device 106. For example, when the host device 106 is a vital signs monitor, the host device electronics 184 operate to monitor vital signs. An example of a host device 106 is illustrated and described in more detail herein with reference to FIG. 6.

Turning now to the divided USB communication device of the dockable instrument assembly 102, the divided USB communication device includes the first portion 152 and the second portion 154. The first portion 152 is included in the portable instrument 110, while the second portion 154 is included in the docking station 112. In some embodiments, the first portion 152 and the second portion 154 collectively operate to communicate with the host device 106 according to a USB communication protocol, but are separately unable to communicate with the host device 106 according to the USB communication protocol.

In this example, the first portion 152 includes a processing device 166 and a serial communication device 168. The processing device 166 is a device capable of processing data instructions, such as a microprocessor. Various other processing devices may also be used including central processing units ("CPUs), microcontrollers, programmable logic devices, field programmable gate arrays, digital signal processing ("DSP") devices, and the like. Processing devices may be of any general variety such as reduced instruction set computing (RISC) devices, complex instruction set computing devices ("CISC"), or specially designed processing devices such as an application-specific integrated circuit ("ASIC") device, for example. In some embodiments, the processing device 166 is shared with the instrument electronics 162.

In some embodiments, the processing device is programmed to send and receive messages in a manner corresponding to the USB communication protocol. The processing device 166 is communicatively coupled to (or part of) the instrument electronics 162 to receive or generate data to be transmitted to the host device 106 from the instrument electronics.

The serial communication device 168 is communicatively coupled to the processing device 166, and operates to communicate data serially between the portable instrument 110 and the docking station 112. Examples of serial communication devices 168 are communication devices that communicate data according to one of the RS-232, RS-485, and RS-422 data communication standards using a serial data communication format. Other embodiments include other serial communication devices, which can operate according to other serial data communication standards, or can utilize a proprietary serial communication protocol. Some embodiments utilize a serial communication device 168 that communicates data across a single electrical conductor, while in other embodiments communication occurs across multiple conductors, such as utilizing differential signaling. Power and ground conductors are also commonly provided between the serial communication device 168 and the second portion 154.

In some embodiments, the serial communication device 168 and the processing device 166 are a single device, or components of a single system.

An advantage of utilizing a serial communication device 168 in the portable instrument 110 is that the serial communication device 168 is typically less expensive than a USB communication device. Serial communication is less complex than USB communication, and therefore the complexity of the portable instrument 110 is also reduced by utilizing serial communication device 168. Additionally, serial communication is less constrained to particular connectors than USB communication, and a wide variety of possible serial connectors can therefore be used. For example, some suitable connectors have lower cost then a typical USB connector.

In typical embodiments, the host device 106 is incapable of communicating directly with the serial communication device 168 (and vice versa), at least through the USB port 134, because such communication is in a non-USB format according to a non-USB data communication protocol. However, the content of messages from the host portable instrument 110 does conform to the USB communication protocol, except for the format in which the messages are transmitted. Similarly, in some embodiments, communications from the host device 106 (and USB communication device 182) that are transmitted through the USB port 134 are not in the serial data communication format according to a serial data communication protocol.

Accordingly, the second portion 154 of the USB communication device 182 is provided, which when coupled with the first portion 152, allows the portable instrument 110 to communicate with the host device 106.

In this example, the second portion 154 includes a serial to USB converter 176. The serial to USB converter 176 operates to convert electrical signals associated with a serial communication (such as from the serial communication device 168) to electrical signals associated with USB communication (such as for delivery to the USB communication device 182). Additionally, the serial to USB converter 176 also operates in the reverse manner, to convert electrical signals associated with USB communication (such as from the USB communication device 182) to electrical signals associated with serial communication.

In some embodiments, the serial to USB converter 176 is or includes a processing device 178. One example of a suitable serial to USB converter 176 is Part No. C8051F327 USB mixed-signal microcontroller available from Silicon Laboratories Inc. of Austin, Tex., along with associated electronics. The mixed-signal microcontroller includes a USB controller for communicating with the USB communication device 182, as well as a UART serial port for communicating with the serial communication device 168.

Figure 3:
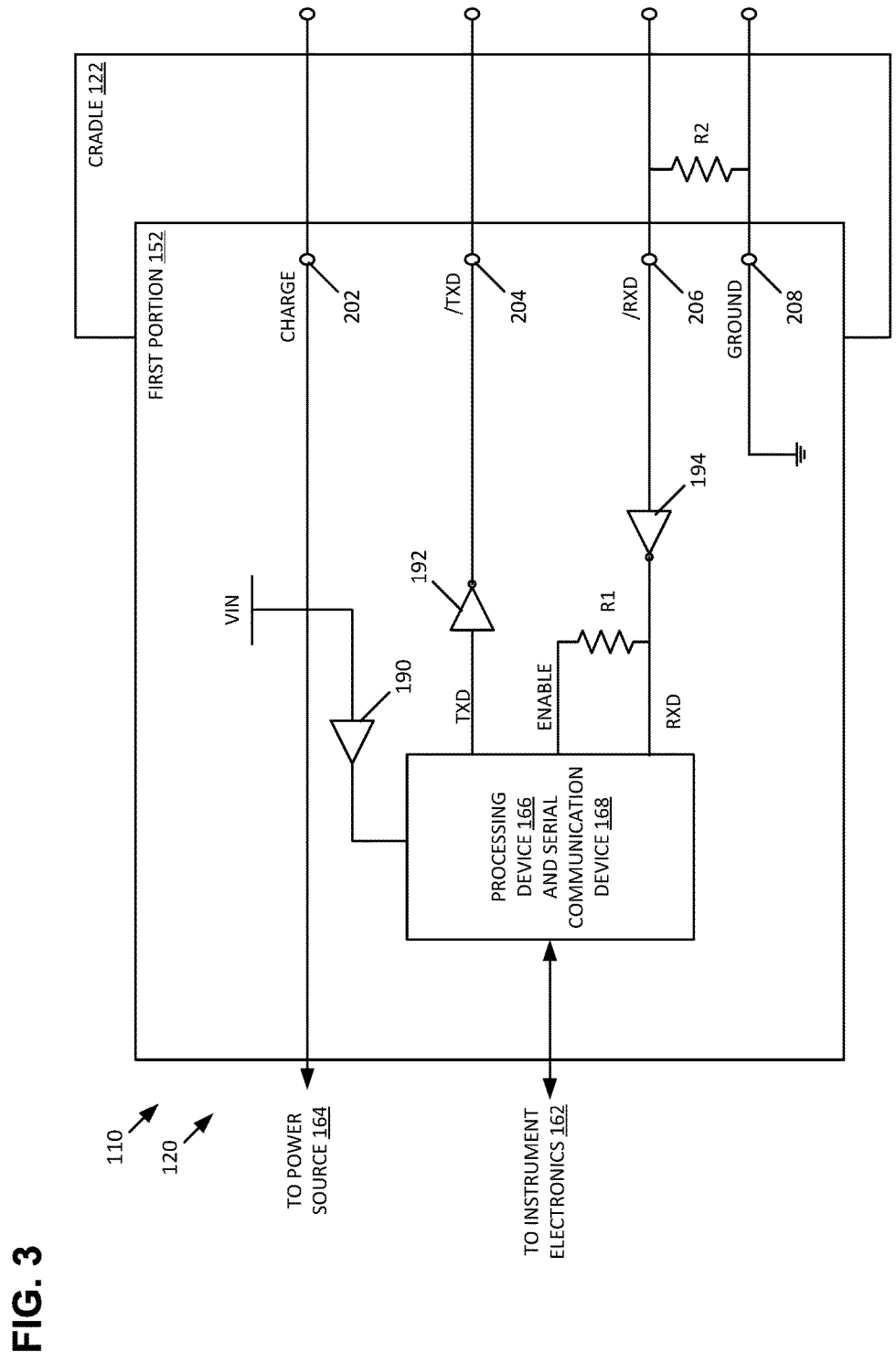
FIG. 3 is a schematic illustrating an example of a first portion of the divided USB communication device, shown in FIG. 1.

FIG. 3 is a schematic block diagram illustrating another example of the first portion 152 of the divided USB communication device, and the cradle 122. The first portion 152 includes the processing device 166 and the serial communication device 168. In this example, the first portion 152 also includes electronic components such as a buffer 190, inverters 192 and 194, and a resistor R1. Electrical connections are made to the cradle 122 and/or the docking station 112 through pins, including the charge pin 202, /TXD pin 204, /RXD pin 206, and ground pin 208. The cradle 122 includes electrical conductors and a resistor R2, and includes pins corresponding to pins 202, 204, 206, and 208 of the first portion 152. In other possible embodiments, the resistor R2 can be included in the first portion 152, or elsewhere in the instrument 120 (shown in FIG. 2).

In some embodiments, the divided USB communication device is designed to conform with one or more design criteria, as follows. First, the first portion 152 should be able to determine when it is inserted or withdrawn from the docking station 112 (shown in FIGS. 2 and 4). Second, the docking station 112 should be able to determine when the portable instrument 110 is in the docking station 112 and when it has been removed. Third, the docking station 112 should not cause USB enumeration to occur at the host device 106 when the portable instrument 110 is not in the docking station 112. Fourth, the externally accessible pins of the portable instrument 110 should have no voltage present (compared with the portable instrument 110 ground) when the portable instrument 110 is not in the docking station 112. Some embodiments confirm with all four design criteria, while other embodiments conform to less than all of the design criteria. Yet other embodiments confirm with none of the four design criteria, or a different set of one or more design criteria.

The charge pin 202 is electrically connected to the power source 164 and receives power from the docking station 112 to recharge power source 164. In some embodiments, the power from the power source 164 is also used to power the processing device 166 and serial communication device 168 through buffer 190.

The /TXD pin 204 is electrically coupled to the TXD pin of the processing device 166 and serial communication device 168 through the inverter 192.

The /RXD pin 206 is electrically coupled to the RXD pin of the processing device 166 and serial communication device 168 through the inverter 194 and also to the ENABLE pin through the resistor R1. In another possible embodiment, the resistor R1 can be coupled to VIN (or another source of a logic high). In either case, the resistor R1 is a pull-up resistor that acts to maintain the RXD pin at a logic high in the absence of a signal or coupling of the pull down resistor R2. However, by coupling the resistor R1 to the ENABLE pin, the processing device 166 can supply the logic high to the ENABLE pin only when performing a check for the docking station 112. This prevents excess leakage current that would continually be flowing through the resistor R1 if R1 is connected to a constant logic high source. In other words, power is saved by connecting the resistor R1 to the ENABLE pin, and selectively setting the ENABLE pin to a logic high only when checking the RXD pin to determine if the portable instrument 110 has been connected with the docking station 112.

The /RXD pin 206 is electrically coupled with the RXD pin through inverter 194, and with the ENABLE pin through resistor R1. Because the /RXD pin 206 is electrically coupled to the RXD and ENABLE pins through inverter 194, the pull-up resistor R1, which operates to pull the RXD pin to a logic high, also operates to pull the/RXD pin 206 to a logic low in the absence of a signal from the docking station 112.

The /RXD pin 206 is also electrically coupled to the resistor R2, at least when the instrument 110 is in the cradle 122. In some embodiments the resistance of R2 is much less than the resistance of R1, such as a factor of 10 times less. As one example, the resistor R1 has a resistance of 100K Ohms, and the resistor R2 has a resistance of 10K Ohms. Other embodiments have other resistances.

The ground pin 208 is electrically coupled to the ground of the portable instrument 110, such as from the power source 164.

As shown, the cradle 122 is configured as a pass-through device, to pass the electrical signals on the pins 202, 204, 206, and 208 to the docking station 112 (when connected to the docking station 112), and vice versa.

The first portion 152 communicates between the instrument electronics 162 and the second portion 154. For example, the first portion 152 is coupled to the instrument electronics 162 to receive data from the instrument electronics 162 to be transferred to the host device 106. The processing device 166 and serial communication device 168 convert the data into a serial data communication format, and transmit the data to the second portion in the serial format. For example, the data is transmitted to the second portion 154 across the TXD and /TXD pin 204 in some embodiments.

Figure 4:
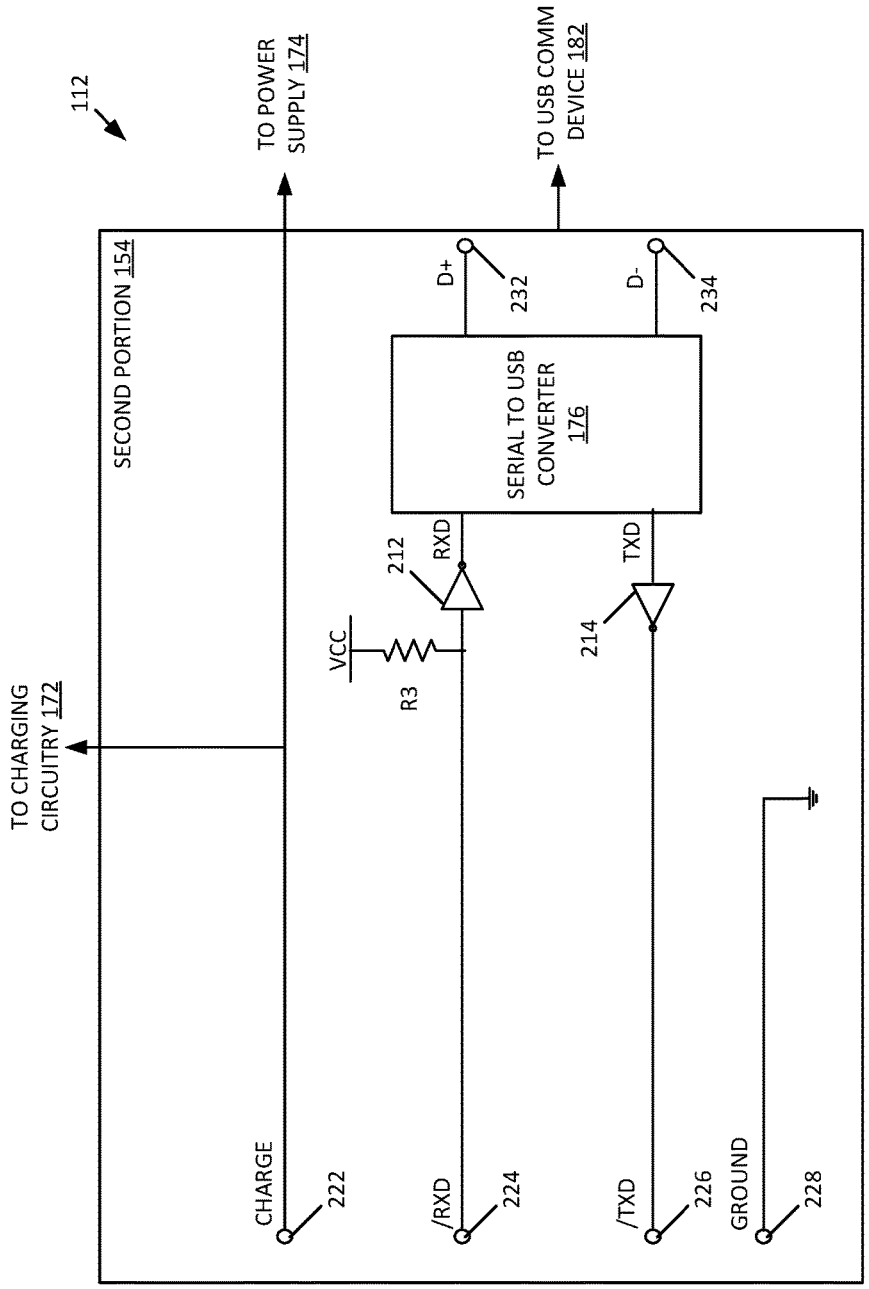
FIG. 4 is a schematic block diagram of an example of a second portion of the divided USB communication device, shown in FIG. 1.

FIG. 4 is a schematic block diagram of an example of the second portion 154 of the divided USB communication device. In this example, the second portion 154 includes the serial to USB converter 176. Additional electronic components are included in some embodiments, such as a pull-up resistor R3 and inverters 212 and 214. The second portion 154 connects with the first portion 152 (or cradle 122) through charge pin 222, /RXD pin 224, /TXD pin 226, and ground pin 228. The second portion 154 connects with the host device 106 (and USB cable 104) through the D+ pin 232 and D- pin 234. Additional pins (such as power and ground pins) are included in some embodiments. Yet other embodiments have fewer or different pins.

The charge pin 222 connects with the charging circuitry 172 to provide power for recharging the power source 164 of the portable instrument 110, when the portable instrument 110 is connected with the docking station 112. The charging circuitry 172 receives power from the power supply 174. In another possible embodiment, the charging circuitry 172 receives power from the USB communication device 182 (through USB cable 104).

The /RXD pin 224 is electrically coupled to a voltage source (VCC) through pull-up resistor R3, and to the RXD pin of the serial to USB converter 176 through inverter 212.

The /TXD pin 226 is electrically coupled to the TXD pin of the serial to USB converter through the inverter 214.

The ground pin 228 is electrically coupled to the electrical ground of the docking station 112.

The second portion 154 communicates between the first portion 152 and the host device 106. For example, data is received in a serial communication format from the first portion 152 through the /RXD pin 224 and the RXD pin. The data is then converted into a USB communication format, and transmitted to the host device through the D+ pin 232 and the D- pin 234 and through the USB cable 104 electrically coupled to the pins 232 and 234. In some embodiments, data is also received from the host device through the D+ pin 232 and the D- pin 234 (and USB cable 104) in the USB communication format, which is then converted into the serial communication format by the serial to USB converter 176, and transmitted through the TXD pin and /TXD pin 226 to the first portion 152.

In some embodiments, the docking station 112 detects when the portable instrument 110 is connected to the docking station 112. In one example, the docking station 112 monitors the RXD pin for a transition that occurs within a predetermined time period (e.g., 40 ms). When the transition is detected, the docking station 112 determines that the portable instrument 110 has been placed into the docking station 112. At this time, the docking station 112 initializes the USB interface causing a USB arrival. The host device 106 detects and recognizes the connection of the portable instrument 110. Even though the docking station 112 was already connected to the host device 106 through the USB cable 104, the USB arrival does not occur until the portable instrument 110 is placed into the docking station. This prevents the host device 106 from attempting to communicate with the docking station 112, for example, before the portable instrument 110 is connected and available to receive the communication.

In some embodiments, the docking station 112 monitors the RXD pin to determine when the portable instrument 110 is removed from the docking station 112. In one example, the portable instrument 110 is determined to be removed from the docking station 112 if the RXD pin remains at a logic high for greater than a predetermined time period (e.g., 40 ms). When this occurs, the second portion 154 determines that the portable instrument 110 has been removed, and resets itself. This causes the host device 106 to recognize a USB device departure, and to de-enumerate. In other words, the host device 106 also acts as though the dockable instrument assembly 102 has been disconnected from the USB port 134 (shown in FIG. 1), even though the docking station 112 remains connected to the USB port 134 through the USB cable 104.

Figure 5:
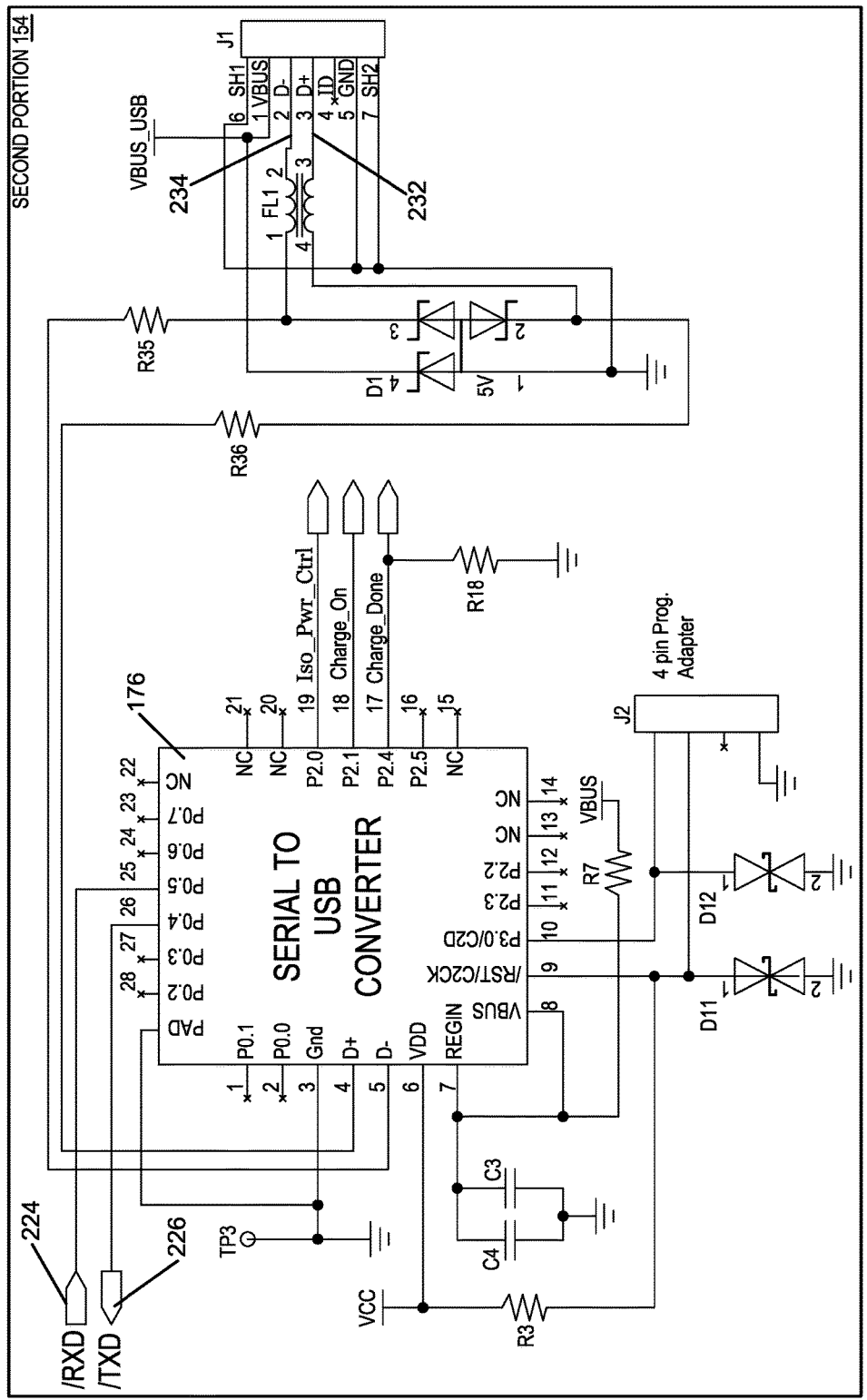
FIG. 5 is a schematic diagram illustrating an example implementation of the second portion of the divided USB communication device, shown in FIG. 4.

FIG. 5 is a schematic diagram illustrating an example implementation of the second portion 154 of the divided USB communication device, such as can be incorporated into the docking station 112.

In this example, the second portion 154 includes the serial to USB converter 176 and associated electronic components, including electrical conductors and connection points. The connection points include the /RXD pin 224, /TXD pin 226, D+ pin 232, and D- pin 234. Other electronic components include resistors R3, R7, R18, R35, and R36, electrostatic discharge (ESD) suppressors D11 and D12, 4 pin programming adapter J2, avalanche diodes D1, capacitors C3 and C4, and transformer FL1. An example of the electrical connections between the USB converter 176 and the various electronic components are illustrated in FIG. 5.

The example implementation shown in FIG. 5 operates in the same manner as the example illustrated in and described with reference to FIG. 4. For example, serial communications between the serial to USB converter 176 and the first portion 152 (shown in FIG. 3) occur through the /RXD pin 224 and the /TXD pin 226. USB communications occur between the serial to USB converter 176 and the host device 106 through the D+ and D− pins 232 and 234.

In this example, the serial to USB converter 176 is the Part No. C8051F327 USB mixed-signal microcontroller. Other embodiments utilize other serial to USB communication devices.

One example of a suitable ESD suppressor (D11 and D12) is the Part No. PGB1010603MR available from Littelfuse, Inc. of Chicago, Ill.

One example of a suitable avalanche diode (D1) package is the Part No. SP0503BAHT Transient Voltage Suppression Avalanche Diode Array, available from Littelfuse, Inc.

The resistors are selected to have resistances and tolerances appropriate for the given implementation. In one example, the resistor R3 is a 3.3K Ohm resistor, the resistor R18 is a 10K Ohm resistor, and the resistors R35 and R36 are 22 Ohm resistors.

The capacitors are also selected to have characteristics appropriate for the given implementation. In one example, the capacitors C3 and C4 are a 1 μF capacitor and a 0.1 μF capacitor, respectively.

The transformer FL1 is coupled to the D+ and D− pins 232 and 234, in some embodiments, which is used for isolation to protect the docking station 112 electronics from any large voltages or voltage spikes that may be received at the USB port 132.

The charge_on and charge_done pins are used in some embodiments by the charging circuitry 172 to determine when to charge the power source 164 of the portable instrument 110.

Figure 6:
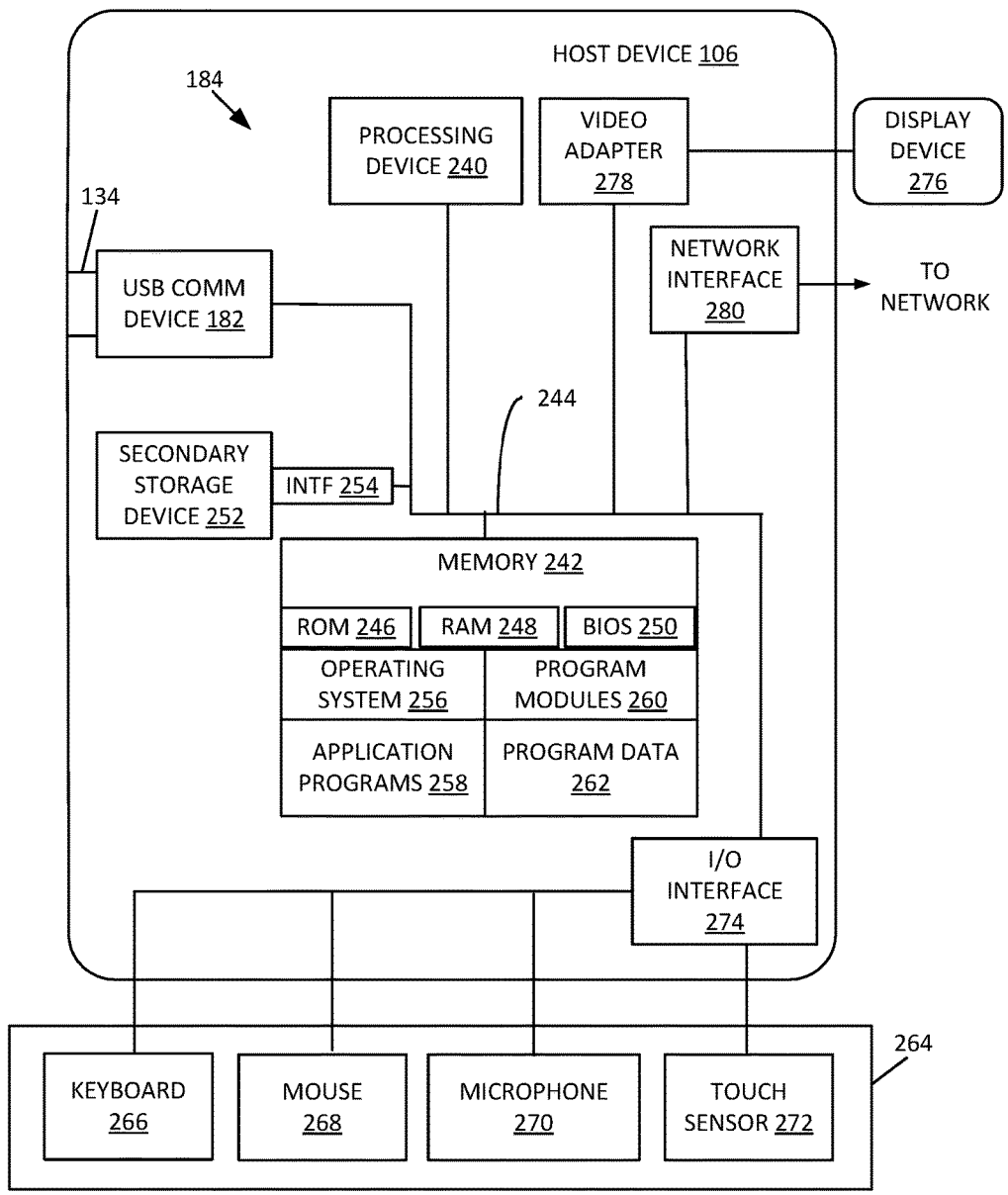
FIG. 6 is a schematic block diagram of an example host device of the USB communication system shown in FIG. 1.

FIG. 6 is a schematic block diagram of an example host device 106.

The host device 106 includes, in some embodiments, at least one processing device 240, such as a central processing unit (CPU). A variety of processing devices are available from a variety of manufacturers, for example, Intel or Advanced Micro Devices. In this example, the host device 106 also includes a system memory 242, and a system bus 244 that couples various system components including the system memory 242 to the processing device 240. The system bus 244 is one of any number of types of bus structures including a memory bus, or memory controller; a peripheral bus; and a local bus using any of a variety of bus architectures.

Examples of devices suitable for the host device 106 include a vital signs monitor, a desktop computer, a laptop computer, a tablet computer, a mobile computing device (such as a smart phone, an iPod® or iPad® mobile digital device, or other mobile devices), or other devices configured to process digital instructions and communicate through a USB communication device 182.

The system memory 242 includes read only memory 246 and random access memory 248. A basic input/output system 250 containing the basic routines that act to transfer information within host device 106, such as during start up, is typically stored in the read only memory 246.

The host device 106 also includes a secondary storage device 252 in some embodiments, such as a hard disk drive, for storing digital data. The secondary storage device 252 is connected to the system bus 244 by a secondary storage interface 254. The secondary storage devices 252 and their associated computer readable media provide nonvolatile storage of computer readable instructions (including application programs and program modules), data structures, and other data for the host device 106.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 252 or memory 242, including an operating system 256, one or more application programs 258, other program modules 260 (such as the software engines described herein), and program data 262. The host device 106 can utilize any suitable operating system, such as Microsoft Windows™, Google Chrome™, Apple OS, and any other operating system suitable for a host device.

In some embodiments, a user provides inputs to the host device 106 through one or more input devices 264. Examples of input devices 264 include a keyboard 266, mouse 268, microphone 270, and touch sensor 272 (such as a touchpad or touch sensitive display). Other embodiments include other input devices 264. The input devices are often connected to the processing device 240 through an input/output interface 274 that is coupled to the system bus 244. These input devices 264 can be connected by any number of input/output interfaces, such as a parallel port, serial port, game port, or a universal serial bus interface (such as available through the USB port 134 and USB communication device 182). Wireless communication between input devices and the interface 274 is possible as well, and includes infrared, BLUETOOTH® wireless technology, 802.11a/b/g/n, cellular, or other radio frequency communication systems in some possible embodiments.

In this example embodiment, a display device 276, such as a monitor, liquid crystal display device, projector, or touch sensitive display device, is also connected to the system bus 244 via an interface, such as a video adapter 278. In addition to the display device 276, the host device 106 can include various other peripheral devices (not shown), such as speakers or a printer.

When used in a local area networking environment or a wide area networking environment (such as the Internet), the host device 106 is typically connected to a data communication network through a network interface 280, such as an Ethernet interface. In another possible embodiment, the host device 106 communicates through a wireless network interface, such as utilizing WIFI, BLUETOOTH, cellular, or other wireless data communication protocols. Other possible embodiments use other communication devices. For example, some embodiments of the host device 106 include a modem.

The host device 106 typically includes at least some form of computer readable media. Computer readable media includes any available media that can be accessed by the host device 106. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the host device 106. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The host device illustrated in FIG. 6 is also an example of programmable electronics, which may include one or more such host devices 106, and when multiple host devices 106 are included, such host devices can be coupled together with a suitable data communication network so as to collectively perform the various functions, methods, or operations disclosed herein.

Figure 7:
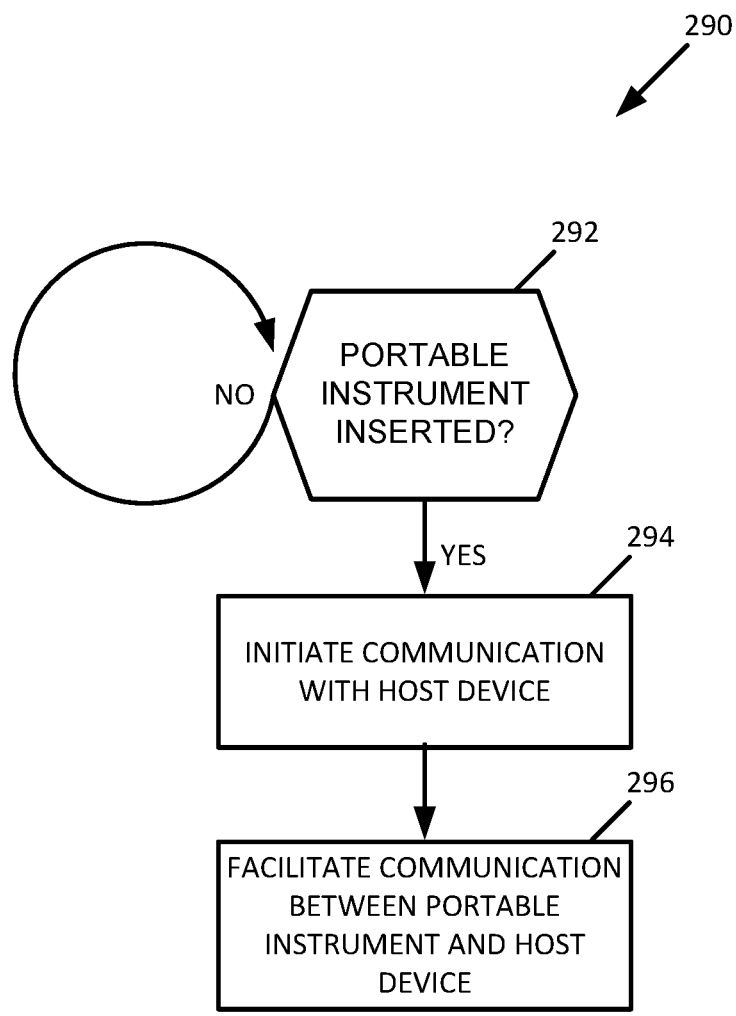
FIG. 7 is a flow chart illustrating an example method of communicating with a USB-enabled host device.

FIG. 7 is a flow chart illustrating an example method 290 of communicating with a USB-enabled host device. In this example, the method includes operations 292, 294, and 296.

The operation 292 is performed to monitor for the insertion of a portable instrument into the docking station 112. The operation 292 continues until the insertion of the portable instrument into the docking station is detected.

After operation 292, the operation 294 is performed to initiate communication with the host device 106. In some embodiments, the initiation of communication alerts the host device to an arrival of the portable instrument, and causes enumeration of the portable instrument 110 by the host device 106.

The operation 296 is performed to facilitate communication between the portable instrument 110 and the host device 106. An example of operation 296 is illustrated in FIG. 8.

Figure 8:
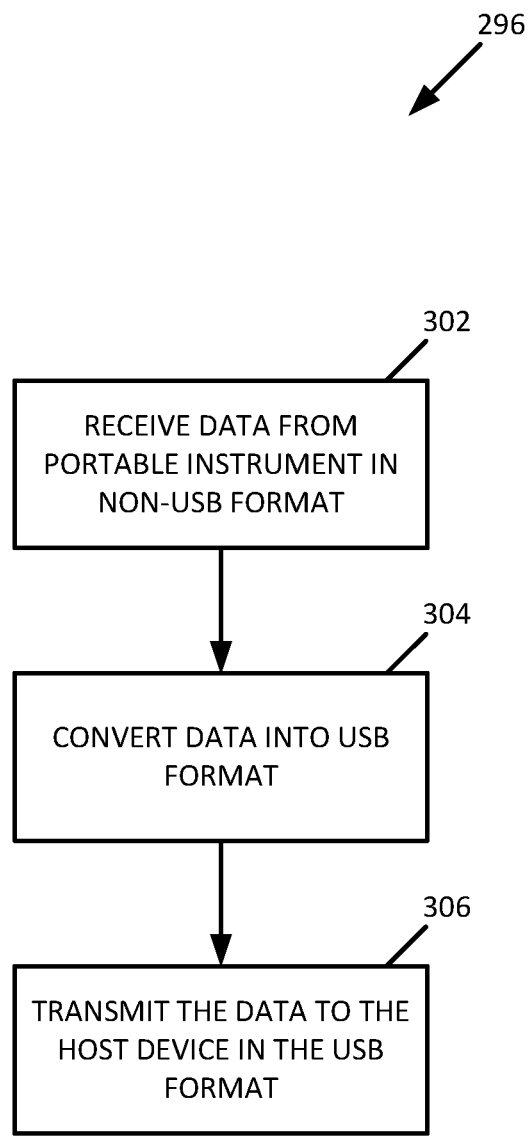
FIG. 8 is a flow chart illustrating an example method of facilitating communication between a portable instrument and a host device.

FIG. 8 is a flow chart illustrating an example method of facilitating communication between the portable instrument 110 and a host device 106. FIG. 8 also illustrates an example of operation 296, shown in FIG. 7. In this example, the method includes operations 302, 304, and 306. In some embodiments, the method and operations are performed by the docking station 112.

The operation 302 is performed to receive data from the portable instrument 110 in a non-USB format.

The operation 304 is performed to convert the data into a USB format.

The operation 306 is performed to transmit the data to the host device 106 in the USB format.

In some embodiments, data communication also occurs from the host device 106 to the portable instrument 110. For example, data is received from the host device in a USB format. The data is converted into a non-USB format, such as a serial data communication format. The data is then transmitted to the portable instrument in the non-USB format.

Figure 9:
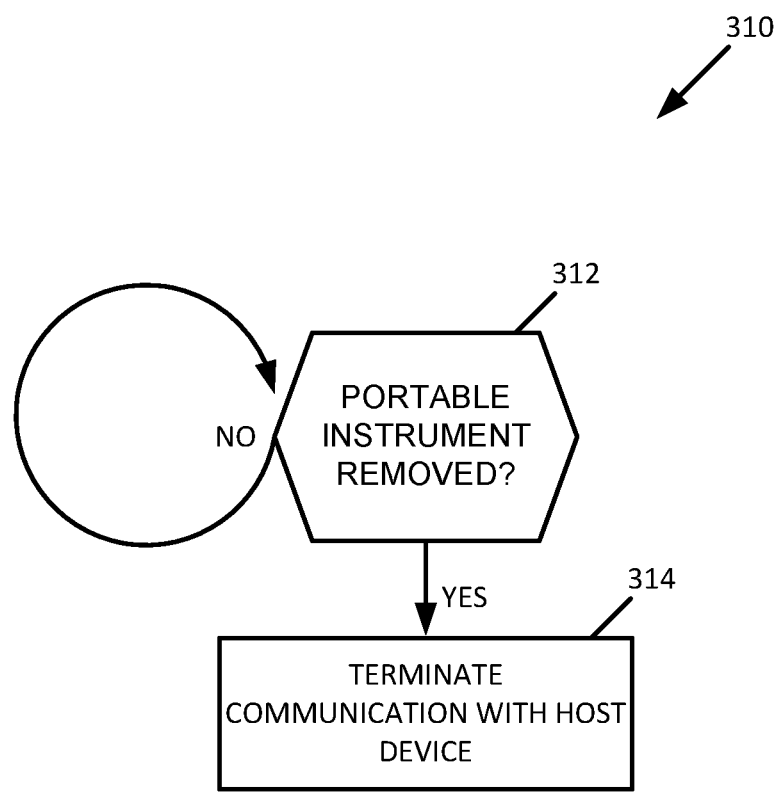
FIG. 9 is a flow chart illustrating a method of terminating communication with a USB-enabled host device.

FIG. 9 is a flow chart illustrating a method 310 of terminating communication with a USB-enabled host device. In this example, the method includes operations 312 and 314.

The operation 312 is performed to monitor for the disconnection and removal of the portable instrument from the docking station 112. Monitoring continues until the disconnection is detected.

The operation 314 is then performed to terminate communication with the host device. In some embodiments, the termination of communication alerts the host device to the departure of the portable instrument, and causes de-enumeration of the portable instrument 110 at the host device 106.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A docking station comprising:
 a housing having a receptacle formed therein, the receptacle sized and configured to receive and support at least a portion of a portable medical instrument and including electrical contacts arranged to electrically connect with the portable medical instrument, wherein the portable medical instrument includes a first portion of a USB communication device adapted to communicate in a serial data communication format; and
 a second portion of the USB communication device enclosed in the housing, the second portion comprising:
  a serial to USB converter arranged in the housing and electrically connected to the electrical contacts, wherein the serial to USB converter is arranged and configured to convert between the serial data communication format and a USB data communication format to facilitate communication between the portable medical instrument and a host device; and
  electronic circuitry that detects the electrical connection of the portable medical instrument with the electrical contacts and initiates the communication with the host device after detecting the electrical connection, which causes enumeration of the portable medical instrument at the host device.

2. The docking station of claim 1, wherein the electronic circuitry further detects the electrical disconnection of the portable medical instrument from the electrical contacts by detecting an absence of a logic signal and terminates the communication with the host device after detecting the electrical disconnection.

3. The docking station of claim 2, wherein the termination of the communication causes de-enumeration of the portable medical instrument at the host device.

4. The docking station of claim 1, wherein the serial to USB converter is part of the electronic circuitry.

5. A portable medical instrument and cradle combination comprising:
 an instrument including:
  instrument electronics adapted to generate data associated with a physiological characteristic of an individual; and
  a first portion of a USB communication device, the first portion comprising:

a processing device, the processing device programmed to send and receive messages including the data; and a serial communication device that receives the messages from the processing device and transmits the messages to a docking station in a non-USB serial data communication format; and a cradle having a receptacle sized to receive at least a portion of the cradle therein, and electrically connected to the instrument when the instrument is in the receptacle, wherein the cradle includes electrical conductors for passing electrical signals from the instrument to the docking station, wherein the portable instrument generates no voltage at the electrical conductors when the instrument and cradle are separated from the docking station.

6. The portable medical instrument and cradle combination of claim 5, wherein the first portion further includes electrical contacts, wherein the first portion determines that the portable instrument is connected to the docking station by detecting a logic level transition that occurs upon electrical connection of the portable instrument to the docking station.

7. The portable medical instrument and cradle combination of claim 5, wherein the non-USB serial data communication format conforms to one of the following serial data communication standards: RS-232, RS-485, and RS-422.

8. The portable medical instrument and cradle combination of claim 5, wherein the portable medical instrument is incapable of direct communication with a USB communication device of a host device through a USB cable.

9. The portable medical instrument and cradle combination of claim 5, wherein the portable medical instrument is an infrared ear thermometer.

10. The portable medical instrument and cradle combination of claim 5, wherein the cradle further comprises at least one pull-down resistor electrically coupled between at least two of the electrical conductors, wherein the instrument detects when it is inserted into the cradle by detecting a voltage change caused at least in part by the electrical coupling between the electrical conductors through the pull-down resistor.

11. A dockable instrument assembly including a divided universal serial bus (USB) communication device configured to communicate with a USB-enabled host device, the dockable instrument assembly comprising:

a portable instrument comprising:
  instrument electronics operable to generate data to be communicated to the host device, the data being associated with a physiological characteristic of an individual; and
  a first portion of the divided USB communication device comprising a serial communication device, wherein the first portion is arranged and configured to receive the data from the instrument electronics and transmit the data in a serial format with the serial communication device; and a docking station comprising:
  a receptacle sized to receive at least a portion of the portable instrument therein;
  a second portion of the divided USB communication device, the second portion comprising a serial to USB converter arranged and configured to:
    detect when the portable instrument is inserted into the receptacle;
    after detecting insertion of the portable instrument into the receptacle, initiate communication with the host device which causes enumeration of the portable instrument at the host device; and
    facilitate communication between the portable instrument and the host device.

12. The dockable instrument assembly of claim 11, wherein to facilitate the communication between the portable instrument and the host device, the serial to USB converter is further arranged and configured to:
  receive the data from the portable instrument in the serial format;
  convert the data into a USB format; and
  transmit the data to the host device in the USB format.

13. A method of communicating with a USB-enabled host device, the method comprising:
  monitoring for insertion of a portable medical instrument into a docking station;
  detecting the insertion of the portable medical instrument into the docking station, the portable medical instrument configured to communicate with the docking station through a non-USB data communication device in a non-USB format;
  after detecting the insertion of the portable medical instrument, initiating communication with the host device to alert the host device to an arrival of the portable medical instrument and cause enumeration of the portable medical instrument at the host device; and
  facilitating communication between the portable medical instrument and the host device.

14. The method of claim 13, wherein facilitating communication between the portable medical instrument and the host device further comprises:
  receiving data from the non-USB data communication device of the portable medical instrument in the non-USB format;
  converting the data into a USB format; and
  transmitting the data to the host device in the USB format.

15. The method of claim 14, wherein transmitting the data to the host device in the USB format occurs through a USB cable.

16. The method of claim 15, wherein the non-USB data communication device is a serial communication device.

17. The method of claim 13, wherein while monitoring for the insertion of the portable medical instrument, the docking station does not trigger device enumeration at the host device.

18. A docking station comprising:
  a housing having a receptacle formed therein, the receptacle sized and configured to receive and support at least a portion of a portable medical instrument and including electrical contacts arranged to electrically connect with the portable medical instrument, wherein the portable medical instrument includes a first portion of a USB communication device adapted to communicate in a serial data communication format; and
  a second portion of the USB communication device enclosed in the housing, the second portion comprising:
    a serial to USB converter arranged in the housing and electrically connected to the electrical contacts, wherein the serial to USB converter is arranged and configured to convert between the serial data communication format and a USB data communication format to facilitate communication between the portable medical instrument and a host device; and
    electronic circuitry that detects the electrical connection of the portable medical instrument with the electrical contacts and initiates the communication with the host device after detecting the electrical connection, and wherein the electronic circuitry further detects the electrical disconnection of the portable medical instrument from the electrical contacts by detecting an absence of a logic signal and terminates the communication with the host device after detecting the electrical disconnection.

* * * * *